United States Patent [19] [11] Patent Number: 4,694,074
Uemura et al. [45] Date of Patent: Sep. 15, 1987

[54] PROCESS FOR THE PURIFICATION OF HBSAG

[75] Inventors: Yahiro Uemura; Takao Ohmura, both of Osaka; Akimasa Ohmizu, Hyogo; Akinori Sumi; Wataru Ohtani, both of Osaka; Yoshitaka Sakanishi, Hyogo; Hiroshi Morise; Hirofumi Arimura, both of Osaka; Tadakazu Suyama, Kyoto, all of Japan

[73] Assignee: Green Cross Corporation, Osaka, Japan

[21] Appl. No.: 792,081

[22] Filed: Oct. 28, 1985

[30] Foreign Application Priority Data

Oct. 26, 1984 [JP] Japan ................................ 59-224116

[51] Int. Cl.$^4$ ...................... A61K 39/29; C12P 21/00; C07K 3/18; C07K 3/28
[52] U.S. Cl. ..................................... 530/417; 424/89; 424/86; 435/68; 435/172.2; 435/172.3; 530/403; 530/404; 530/405; 530/415; 530/806; 530/808
[58] Field of Search ....................... 260/112 R, 112 B; 424/86, 101, 89; 435/68, 172.3, 172.2, 240, 241; 530/403, 404, 405, 417, 808, 806

[56] References Cited

U.S. PATENT DOCUMENTS

| 3,951,937 | 4/1976 | Vnek et al. ..................... 260/112 B |
| 4,113,712 | 9/1978 | Funakoshi ....................... 260/112 R |
| 4,138,287 | 2/1979 | Andersson et al. .............. 424/89 X |
| 4,162,192 | 7/1979 | Mizuno et al. .................... 424/89 X |
| 4,168,300 | 9/1979 | Andersson et al. ......... 260/112 B X |
| 4,434,093 | 2/1984 | Zolton et al. .................... 260/112 B |
| 4,442,505 | 4/1984 | Hamer et al. .................... 424/89 X |
| 4,515,714 | 5/1985 | Kawahara et al. ............. 260/112 R |
| 4,547,368 | 10/1985 | Tabor et al. .......................... 424/89 |
| 4,563,423 | 1/1986 | Murray et al. ....................... 435/68 |
| 4,599,230 | 7/1986 | Milich et al. .................... 530/806 X |
| 4,612,283 | 9/1986 | Sugahara et al. .............. 530/404 X |

FOREIGN PATENT DOCUMENTS

| 0020251 | 12/1980 | European Pat. Off. . |
| 0100561 | 2/1984 | European Pat. Off. . |
| 5663995 | 5/1981 | Japan . |
| 883549 | 11/1961 | United Kingdom .................. 424/85 |

Primary Examiner—Howard E. Schain
Attorney, Agent, or Firm—Sughrue, Mion, Zinn, Macpeak & Seas

[57] ABSTRACT

A process for the purification of HBsAg is disclosed, which comprises adsorbing specifically on a carrier, in the presence of an inorganic salt in an amount of 5 to 25 W/V %, an HBsAg obtained by gene engineering.

6 Claims, No Drawings

PROCESS FOR THE PURIFICATION OF HBSAG

BACKGROUND OF THE INVENTION

The present invention relates to a process for the purification of hepatitis B antigen (hereinafter referred to HBsAg) obtained by gene engineering.

HBsAg is the main ingredient of hepatitis B vaccine.

Hepatitis B vaccine was developed and put to practical use, by isolation of HBsAg particles, inactivation of the HBsAg by formalin treatment or the like, and the subsequent addition to the inactivated HBsAg of alum gel, as adjuvant, to elevate the immunogenicity of HBsAg.

With the hepatitis B vaccine thus prepared, it is possible not only to prevent infection and appearance of hepatitis B, but also to exterminate hepatitis B, because the vaccine is effective also in inhibiting generation of infectious carriers.

However, there are some problems in the production of hepatitis B vaccine. The first problem is that the supply of vaccine is restricted because of the starting material for HBsAg relies on the carrier's blood. The second problem is that a safety test using chimpanzees, the only animals capable of being infected with hepatitis B, is required because infectious hepatitis B virus (HBV) is contained in the carrier's blood, though its amount is minor.

In order to overcome such problems in the production of a vaccine, a techhnique of gene engineering was introduced.

The technique of DNA recombination was initiated by a process of combining a heterogenic DNA with a phage or a plasmid DNA and multiplying the recombinant DNA by means of *Escherichia coli*. Then the technique developed into the determination of the total base sequence of HBV-DNA, the identification of the HBsAg gene to be used as a vaccine, the phenotypic expression with *Escherichia coli* and the reproduction of HBsAg with yeast.

For instance, yeast-derived HBsAg (y-HBsAg) consists, according to SDS-polyacrylamide gel electrophoresis, only of polypeptides having a molecular weight 23,000 to 25,000 Daltons which corresponds with the unglycosylated polypeptides of human-derived HBsAg (h-HBsAg). Further, y-HBsAg has the same diameter of 22 nm as h-HBsAg, and its buoyant density in cesium chloride solution is the same as that of h-HBsAg.

In order to overcome the above-described problems in the production of hepatitis B vaccine, a process of obtaining a large amount of HBsAg by means of the technique of gene engineering and preparing a vaccine by highly purifying the HBsAg is now being developed.

However, when hepatitis B vaccine is prepared by purification of HBsAg obtained from cells resulting from gene engineering, a problem arises as to how to remove the ingredients of the cell body, which consists mainly of proteins and are present as contaminates in the starting materials. These contaminants cannot be removed well by conventional purification processes for plasma-derived HBsAg.

SUMMARY OF THE INVENTION

Under such technical circumstances, the inventors of the present invention have found as a result of earnest investigations, a process for efficiently purifying the HBsAg produced inside or outside the cell body resulting from gene engineering, and completed this invention.

Thus, the present invention provides a process for highly purifying HBsAg, which comprises adsorbing specifically on a carrier, in the presence of an inorganic salt in a relatively high concentration, an HBsAg obtained by gene engineering.

DETAILED DESCRIPTION OF THE INVENTION

There is no special limitation on the HBsAg used in the present invention, as long as it is one prepared by, or resulting from, gene engineering. Therefore, any HBsAg extract fraction obtained by treating an HBsAg-producing cell body (such as *Escherichia coli*, yeast, *Bacillus subtilis* or the like) resulting from gene engineering, in accordance with a known method such as freezing and thawing method, glass bead method, high pressure method, ultrasonication method, enzyme treatment method or the like, or any fraction obtained by partially purifying the extract fraction in accordance with a known method such as various fractionation methods, adsorption chromatography, affinity chromatography, gel filtration, density-gradient centrifugation method, dialysis or the like, can be used as the HBsAg (cf. Japanese Patent Application (OPI) No. 115189/1984, etc.).

As examples of the inorganic salt used in the present invention, there can be mentioned sulfates, phosphates, chlorides and the like, as anions, and ammonium salts, sodium salts, potassium salts and the like, as cations. Preferably, ammonium sulfate, sodium sulfate, sodium chloride or a phosphate compound (such as sodium dihydrogen phosphate, potassium dihydrogen phosphate, disodium hydrogen phosphate or the like) is used as the inorganic salt. Of these, ammonium sulfate, sodium sulfate and sodium chloride are particularly preferred.

Such inorganic salt is added preferably in a cencentration of 5 to 25 W/V %, more preferably 5 to 10 W/V %. When the concentration is lower than 5 W/V %, HBsAg is not adsorbed on the carrier. When the concentration is higher than 25 W/V %, contaminating proteins are adsorbed on the carrier along with HBsAg. Thus, a concentration lower than 5 W/V % or higher than 25 W/V % is not suitable.

As the carrier used in the present invention, fixing carriers (carriers of fixation) having hydrophobic groups are suitable. Amino acid copolymer, cellulose, agarose, dextran, polyacrylic amide or the like, preferably agarose, can be used as the fixing carrier, and a phenylalanine residue, an alkyl group containing 2 to 8 carbon atoms (e.g., ethyl, propyl, butyl, pentyl, hexyl, heptyl and octyl, with ethyl, propyl and butyl being preferred), a phenyl group or the like can be used as the hydrophobic group. Of these, phenylalanine residue, phenyl and ethyl are preferred.

Fixing of the hydrophobic group can be performed in the conventional manner (e.g., *Nature*, 214: 1302–1304 (1967) and *Proc. Nat. Acad. Sci. U.S.A.*, 61: 636–646 (1968)). For instance, a fixing phenylalanine can be obtained by mixing Sepharose 4B activated by cyanogen bromide with a phenylalanine solution and continuing the reaction at room temperature for 16 hours.

By using the carrier thus obtained, HBsAg can be obtained in good yield and high purity.

The adsorption chromatography of HBsAg according to the present invention is performed as described below. The chromatography in the present invention may be performed by either a column process or a batch process.

To perform the chromtography, an inorganic salt is added to a crude HBsAg solution and the concentration of the inorganic salt in the resulting solution is adjusted to 5 to 25 W/V %. Then the solution is brought into contact with a carrier equilibrated with an inorganic salt solution of the same concentration, whereby the HBsAg is adsorbed on the carrier. Thereafter, the carrier is washed with 2 to 5 times the amount of the same inorganic salt solution to wash away contaminating proteins not adsorbed, and then the HBsAg adsorbed is eluted with a buffer solution (for example, a phosphate buffer solution) containing 5 to 20 V/V % (preferably, 10 V/V %) of ethanol and having a pH of 6 to 8. The eluent is used in an amount of about 1 to 2 ml per ml of the carrier.

The eluate fraction thus obtained is further purified highly by known purification methods (e.g., Japanese Patent Application (OPI) No. 115189/1984). The fraction can be provided also as HB vaccine for clinical use, by applying thereto known pharmaceutical technique (e.g., Japanese Patent Application (OPI) No. 101426).

The HBsAg purified by the process of the present invention shows a single band corresponding to a molecular weight of 25,000 in SDS (sodium dodecyl sulfate)-polyacrylamide gel electrophoresis and does not contain any contaminating pyrogen. When an animal is immunized with the purified HBsAg, the animal produces a strong HBs antibody response.

HBsAg obtained according to the present invention is an HBsAg of high quality containing very few contaminating substances. By the purification process of the present invention, those contaminating proteins of cell body origin, which cannot be removed by conventional purification processes for plasma-derived HBsAg, can be removed. Therefore, it is possible to prepare HB vaccine having the same excellent safety as conventional products, even when an HBsAg obtained through gene engineering is used.

The present invention is further explained in detail by giving Examples which, however, do not constitute any restrictin on the present invention.

EXAMPLE 1

In 1 liter of 0.1M phosphate buffer solution was suspended 1 Kg of HBs antigen-producing yeast, and the pH of the suspension was adjusted at 10. Then, HBsAg was extracted from the suspension by ultra-sonication. In the course of the extraction, the pH was adjusted again at 10. After the ultra-sonication, precipitates were removed by centrifugation at 10,000 g for 20 minutes, to obtain the extract.

After adjusting the pH of the extract thus obtained at 7.2, ammonium sulfate was added to the extract in an amount of 70 g per liter of the latter and then the extract was poured into a column of phenylalanine/Sepharose 4B prepared separately, to make adsorbed HBs antigen. After washing well with an ammonium sulfate solution of the same concentration as mentioned above to remove contaminating substances, HBs antigen was eluted by means of a 0.1M phosphate buffer solution (pH 7.2) containing 10 V/V % of ethanol. The degree of purification of HBs antigen in the eluate was 280 times that of the extract [HBsAg specific activity (RPHA Titer/A 280) was measured according to the RPHA method] and the yield of recovery was 70% (Japan. J. Exp. Med., 39 (6): 615–620 (1969)).

The preparation of phenylalanine/Sepharose 4B was effected by adding phenylalanine to Sepharose 4B activated with cyanogen bromide and continuing the reaction at room temperature for 16 hours.

In the same manner, various inorganic salts were added to the stock extracts, and each extract was poured into the phenylalanine/Sepharose 4B column equilibrated with the corresponding inorganic salt solution of the same concentration. After washing well, HBs antigen was eluted by means of 0.1M phosphate buffer solution (pH 7.2) containing 10 V/V % of ethanol. The HBsAg specific activity (RPHA Titer/A 280) of each eluate fraction was measured. The results obtained are shown in Table 1.

TABLE 1

| Inorganic Salt | | | | |
|---|---|---|---|---|
| Sort | Concentration (w/v %) | RPHA Titer | A 280 | RPHA Titer/ A280 |
| Stock Extract | | 1:1024 (100) | 48 | 21.3 |
| ulfate | | (30) | | |
| " | 7.0 | 1:512 (70) | 0.086 | 5953 |
| " | 10 | 1:512 (80) | 0.102 | 5020 |
| " | 20 | 1:512 (80) | 0.128 | 4000 |
| " | 30 | 1:512 (80) | 0.152 | 3368 |
| Sodium Sulfate | 5.0 | 1:512 (65) | 0.096 | 5333 |
| Sodium Chloride | 5.0 | 1:512 (25) | 0.050 | 5120 |
| Sodium Chloride | 20 | 1:512 (75) | 0.098 | 5224 |

*The yield of eluate recovered is shown in parentheses.

Aerosil was added to the extract obtained in the same manner as Example 1 in an amount of 2 W/V %, HBs antigen was be adsorbed, and after washing with isotonic sodium chloride solution HBs antigen was eluted by means of 0.5M sodium chloride solution (pH 9.3). The yield of HBs antigen recovered in this elution process was 100%. Ammonium sulfate was added to the eluate in an amount of 60 g per liter of the latter, and HBs antigen was purified by means of phenylalanine/Sepharose 4B in the same manner as Example 1.

The degree of purification of HBs antigen in the eluate was 5.2 times that of the Aerosil extract, and the yield of recovery was 80%.

EXAMPLE 3

Ammonium sulfate (final concentration: 6.8 W/V %) was added to a stock extract obtained from HBsAg-producing yeast, and the extract was poured into a column of various hydrophobic groups (ligand)/Sepharose 4B equilibrated with the inorganic salt solution of the same concentration. After washing well, HBs antigen was eluted by means of 0.1M phosphate buffer solution (pH 8.0) containing 10 V/V % of ethanol. The HBsAg specific activity (RPHA Titer/A 280) of each eluate fraction was measured. The results obtained are shown in Table 2.

TABLE 2

| Ligand | Yield of Recovery | RPHA Titer | A 280 | RPHA Titer/ A 280 |
|---|---|---|---|---|
| Stock Extract | 100% | 1:512 | 23.1 | 22.2 |
| Phenylalanine | 84% | 1:4096 | 0.74 | 5535 |

TABLE 2-continued

| Ligand | Yield of Recovery | RPHA Titer | A 280 | RPHA Titer/ A 280 |
|---|---|---|---|---|
| Phenyl | 59% | 1:2048 | 0.41 | 4995 |
| Ethyl | 31% | 1:2048 | 0.40 | 5120 |
| Butyl | 30% | 1:2048 | 0.46 | 4452 |
| Hexyl | 25% | 1:2048 | 0.74 | 4357 |
| Octyl | 24% | 1:1024 | 0.25 | 4096 |

While the invention has been described in detail and with reference to specific embodiments thereof, it will be apparent to one skilled in the art that various changes and modifications can be made therein without departing from the spirit and scope thereof.

What is claimed is:

1. A process for the purification of HBsAg obtained by DNA recombination, which comprises adding an inorganic salt to a crude HBsAg solution, said HBsAg having been obtained by DNA recombination, in a concentration so that the resultant HBsAg solution has an inorganic salt concentration of five to twenty-five W/V percent, bringing the resultant solution into contact with a fixing carrier having hydrophobic groups selected from the group consisting of a phenylalanine residue, an alkyl group containing two to eight carbon atoms and a phenyl group, said carrier having been equilibrated with an inorganic salt solution of the same concentration as the resultant HBsAg solution, to adsorb thereon HBsAg with a solution of the inorganic salt to wash away contaminating free proteins and eluting the HBsAg with a buffer solution.

2. The process as claimed in claim 1, wherein the hydrophobic group is selected from the group consisting of a phenylalanine residue, an alkyl group containing 2 to 4 carbon atoms and a phenyl group.

3. The process as claimed in claim 1, wherein the inorganic salt is consisting of at least one anion selected from the group consisting of sulfate, phosphate and chloride, and at least one cation selected from the group consisting of ammonium, sodium and potassium.

4. The process as claimed in claim 3, wherein the inorganic salt is ammonium sulfate, sodium sulfate, sodium chloride, or a phosphate compound.

5. The process as claimed in claim 1, wherein the fixing carrier is selected from the group consisting of an amino acid polymer, cellulose, agarose, dextran and polyacrylic amide.

6. The process as claimed in claim 1, wherein the buffer solution for elution contains 5 to 20 V/V% of ethanol and has a pH of 6 to 8 or is a phosphate buffer solution.

* * * * *